(12) United States Patent
Peng et al.

(10) Patent No.: US 9,440,935 B2
(45) Date of Patent: Sep. 13, 2016

(54) PROCESS FOR PRODUCING 2-PHENYL-1,3-BENZOXAZOLES

(71) Applicant: DSM IP ASSETS B.V., Heerlen (NL)

(72) Inventors: Kun Peng, Basel (CH); Zheng-Chuan Feng, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/901,155

(22) PCT Filed: Jun. 25, 2014

(86) PCT No.: PCT/EP2014/063318
§ 371 (c)(1),
(2) Date: Dec. 28, 2015

(87) PCT Pub. No.: WO2014/207001
PCT Pub. Date: Dec. 31, 2014

(65) Prior Publication Data
US 2016/0185738 A1    Jun. 30, 2016

(30) Foreign Application Priority Data

Jun. 27, 2013   (WO) ................ PCT/CN2013/000771

(51) Int. Cl.
*C07D 263/57*   (2006.01)
(52) U.S. Cl.
CPC .................. *C07D 263/57* (2013.01)

(58) Field of Classification Search
None
See application file for complete search history.

(56) References Cited

PUBLICATIONS

Ghodbane et al., "Facile Access to Highly Fluorescent Nanofibers and Microcrystals via Reprecipitation of 2-Phenyl-benzoxazole Derivatives", *Langmuir*, vol. 28, No. 1, Jan. 10, 2012, pp. 855-863.
Johnson et al., "Biochemical and Structural Evaluation of Highly Selective 2-Arylbenzoxazole-Based Transthyretin Amyloidogenesis Inhibitors", *Journal of Medicinal Chemistry*, vol. 51, No. 2, Jan. 1, 2008, pp. 260-270.
International Search Report for PCT/EP2014/063318, mailed Aug. 6, 2014, four pages.
Büttner et al, *Synthesis and biological evaluation of SANT-2 and analogues as inhibitors of the hedgehog signaling pathway*, Bioorg. Med. Chem. 17 (2009) 4943-4954.

*Primary Examiner* — Kamal Saeed
(74) *Attorney, Agent, or Firm* — Nixon & Vanderhye P.C.

(57) ABSTRACT

The present invention relates to a novel method for producing 2-phenyl-1,3-benzoxazoles of formula (I).

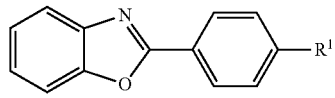

14 Claims, No Drawings

PROCESS FOR PRODUCING 2-PHENYL-1,3-BENZOXAZOLES

This application is the U.S. national phase of International Application No. PCT/EP2014/063318 filed 25 Jun. 2014 which designated the U.S. and claims priority to International Application No. PCT/CN2013/000771 filed 27 Jun. 2013, the entire contents of each of which are hereby incorporated by reference.

The present invention relates to a novel method for producing 2-phenyl-1,3-benzoxazoles.

Many processes for the preparation of 2-phenyl-1,3-benzoxazoles are disclosed in the prior art such as reacting an ortho-hydroxy-aminobenzene with a benzoic acid or a benzoyl chloride in the presence of a catalyst or assistant having a dehydrating action or favoring dehydration such as, for example, boric acid, p-toluenesulphonic acid, a phosphoric acid, sulphuric acid or the like.

These processes, however, either result in low yields or are difficult to scale up in an economic and efficient way e.g. due to the large amount of phosphoric waste and/or elaborate purification steps in order to eliminate discoloration and by-products. Thus, there is an ongoing need for a process for the preparation of 2-phenyl-1,3-benzoxazoles which is easy to carry out and affords economic advantages as a result of high yield and purity and low discoloration.

Thus, it is an object of the present invention to provide a process for the preparation of 2-phenyl-1,3-benzoxazoles which can easily be carried out, also in large scale production, and leads to colorless products in high purities and yields.

It has been found that this object is achieved by a process for producing 2-phenyl-1,3-benzoxazoles of formula (I),

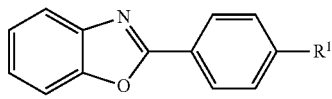
(I)

wherein
$R^1$ is hydrogen, $C_1$-$C_6$-alkyl, halogen, OH or $OR^2$; and
$R^2$ is $C_1$-$C_6$-alkyl, propargyl or allyl said process comprising the steps of
(i) reacting 2-aminophenol (II) with a benzoyl chloride of formula (III) to the amide of formula (IV)

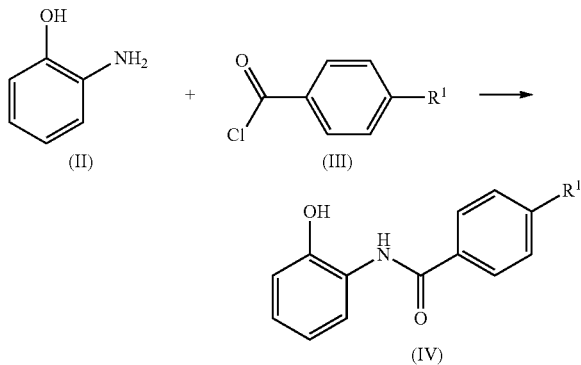

followed by (ii) cyclisation of the amide (IV) to 2-phenyl-1,3-benzoxazol of formula (I), characterized in that step (i) is carried out in an inert organic solvent in the presence of at least 0.75 mole-equivalent of sodium hydrogen carbonate or potassium hydrogen carbonate based on the benzoyl chloride of formula (III).

Suitable $C_1$-$C_6$-alkyl radicals which may be mentioned for $R^1$ are linear or branched $C_1$-$C_6$-alkyl radicals such as methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl.

Suitable halogen radicals encompass fluor, chlor and brom, preferably chlor or fluor, most preferably fluor.

In all embodiments of the present invention preferably $R^1$ denotes to a linear $C_1$-$C_4$-alkyl radical, to $OR^2$ wherein $R^2$ is a propargyl or an allyl radical or to a fluor radical. Most preferably in all embodiment of the present invention $R^1$ denotes to a fluor radical.

The term inert solvent refers to any solvent that does not react or interact in any way with the reagents of the process of the present invention. Such solvents are well known to a person skilled in the art and encompass e.g. hydrocarbon solvents (i.e. organic solvents, molecules of which consist only of hydrogen and carbon atoms) such as for example benzene, toluene, kerosene, xylene, hexane, cyclohexane, methylcyclohexane or other petroleum derivatives, or linear or cyclic ethers such as for example diethyl ether, methyl t-butyl ether (MTBE), dioxane, tetrahydrofurane or 2-methyl-tetrahydrofurane.

Particular suitable solvents in step (i) of the present invention are aromatic hydrocarbons or cyclic ethers such as in particular toluene, xylene, dioxane, tetrahydrofuran or 2-methyltetrahydrofurane as well as mixtures thereof. The most preferred solvent in step (i) in all embodiments of the present invention is 2-methyltetrahydrofuran.

The amount of solvent in step (i) is not critical however is preferably selected such that the amount of the benzoyl chloride of formula (III) is selected in the range of 0.001-2 g/ml solvent, preferably in the range of 0.01-1 g/ml solvent, most preferably in the range of 0.05-0.5 g/ml solvent.

The amount of sodium or potassium hydrogen carbonate is preferably selected in the range of 0.75-1.5 mole-equivalent based on the amount of benzoyl chloride of formula (III). More preferably the amount sodium or potassium hydrogen carbonate is selected in the range of 0.8-1.3, such as most preferably in the range of 0.9-1.2 mole-equivalent, such as e.g. in the range of 1.0-1.2 mole-equivalent.

In all embodiments of the present invention the use of sodium hydrogen carbonate ($NaHCO_3$) is particularly preferred.

The mole ratio of aminophenol (II) to benzoyl chloride (III) is preferably selected in the range of 0.75-1.25, such as more preferably in the range of 0.9-1.1. Most preferably equal molar amounts of aminophenol (II) and benzoyl chloride (III) are used.

The temperature in step (i) might vary in a broad range such as from −10 to 150° C. Preferably, the temperature in step (i) is however selected in the range of 0 to 40° C., more preferably in the range of 5 to 30° C., most preferably in the range of 10 to 20° C.

In a particular preferred embodiment according to the present invention the molar ratio of aminophenol (II) to the benzoylchloride (III) is selected in the range of 0.9-1.1, sodium hydrogen carbonate is used in an amount selected in the range of 0.9-1.2 mole-equivalent based on the benzoyl chloride (III) and the inert solvent is selected from dioxane, toluene, tetrahydrofuran or 2-methyltetrahydrofuran. Even more preferably the inert solvent is 2-methyltetrahydrofuran and the reaction is carried out at a temperature selected in the range of 10 to 20° C. as this leads to particular good yields and purities.

In all embodiments of the present invention it is preferred that the amide of formula (IV) is isolated before the cyclization step. Thus, in a preferred embodiment, the inert solvent of step (i) is evaporated after quenching of the reaction mixture with water, phase separation and optionally washing of the organic phase comprising the amide (IV) with water and/or an aqueous acidic solution such as with 1N $H_2SO_4$. Alternatively, if the amide (IV) precipitates in the used insert solvent the respective amide (IV) could also be isolated by filtration.

The evaporation of the solvent can be done according to standard methods known to a person in the art by applying vacuum and/or heat. Preferably the solvent is removed by evaporation by applying vacuum and heat, such as at temperatures selected in the range of 50 to 150° C., preferably in the range of 60 to 120° C., most preferably in the range of 65 to 115° C. In case of the use of a cyclic ether as inert solvent an aromatic hydrocarbon solvent such as in particular toluene can be used as azeotrop for complete evaporation the cyclic ether. A sign that the cyclic ether is completely removed when using toluene is when the temperature reaches steadily 110° C. at normal pressure.

The cyclization step (ii) to the 2-phenyl-1,3-benzoxazol of formula (I) is preferably performed in a solvent which forms an azeotrop with water such as most preferably in toluene or xylene.

The cyclization takes place in the presence of an acidic catalyst. Acid catalysts which may be used are, for example, HCl, $H_2SO_4$, $HNO_3$, phosphoric acid, sulfonic acids, such as benzenesulfonic acid, p-toluenesulfonic acid (p-TsOH), methanesulfonic acid (MeSOH) or mixtures of these acids, but also sulfonic acid group-containing ion exchangers, such as, for example, Lewatits S100 (Bayer). Preferred acidic catalysts according to the present invention are methanesulfonic acid and p-toluenesulfonic acid as the use of these catalysts results in the highest yields, in particular in toluene and xylene.

The amount of acidic catalyst is preferably selected in the range of 0.05-2 mole equivalents based on the amide (IV). Preferably the amount of the acidic catalyst is selected in the range of 0.1-0.5 mole equivalent, most preferably in the range of 0.15-0.35 mole equivalent based on the amide (IV).

The amount of solvent in the cyclization step (ii) is preferably selected such that the concentration of the amide (IV) is in the range of 0.001-2 g/ml solvent, preferably in the range of 0.01-1 g/ml solvent, most preferably in the range of 0.1-0.5 g/ml.

In a particular preferred embodiment for the cyclization the concentration of the amide (IV) in toluene is selected in the range of 0.2-0.4 g/ml in the presence of 0.2-0.3 mole-equivalents of p-toluenesulfonic acid.

It is furthermore particular advantageous if the reaction water formed during cyclization is continuously removed by azeotrop distillation to further increase the yield.

Best results are used if the cyclization is carried out in toluene as inert solvent, and the acid catalyst is selected from p-toluenesulfonic acid or methanesulfonic acid in an amount of 0.15-0.35 mole equivalents based on the amide (IV). To increase the yield, it is furthermore advantageous if the reaction water formed during the cyclization is removed by azeotropic distillation.

The reaction temperature in the cyclization step is preferably selected in the range of 90 to 130° C., more preferably in the range of 100 to 120° C.

In another embodiment of the present invention, the process according to the present invention may further include a decolorization step. Thus, when the cyclization is complete the reaction mixture is cooled, washed with water and/or an aqueous basic solution such as with an aqueous NaOH solution and the 2-phenyl-1,3-benzoxazole of formula (I) is isolated after separating off the aqueous phase. Afterwards the resulting 2-phenyl-1,3-benzoxazole of formula (I) is dissolved in a suitable solvent which is preferably selected from an aliphatic hydrocarbons solvent such as most preferably form hexane, cyclohexane or heptane and treated with a suitable adsorbent.

Suitable adsorbents used in the decolorization step are generally solid substances which, due to their large surface area, are able to selectively adsorb impurities from liquid mixtures at their interface. Preference is given to adsorbents chosen from the group consisting of activated carbons, aluminum oxides, zeolites and silica gels. Particularly preferred adsorbents are activated carbons and silica gels.

Of the aluminum oxides, basic, neutral or else acidic aluminum oxides may be used. Advantageously, the "active" aluminum oxides, which are obtained, for example, via thermally after-treated aluminum hydroxide gels or by calcination from [alpha]-aluminum hydroxide, are used.

Of the zeolites, the synthetic zeolites are of particular interest as adsorbent. Details on the composition and structure of these zeolites are given in the CD Römpp Chemie Lexikon-Version 1.0, keyword: zeolites, Stuttgart/New York: Georg Thieme Verlag 1995 and the literature cited therein.

The silica gels suitable as adsorbents are described, inter alia, in the CD Rompp Chemie Lexikon-Version 1.0, keyword: silica gels, Stuttgart/New York: Georg Thieme Verlag 1995 and the literature cited therein. Preferred silica gels are silica gel 60 from Merck, Darmstadt and silica gel 123 from Grace.

In a preferred embodiment the decolorization of the 2-phenyl-1,3-benzoxazole of formula (I) is done by treatment with activated carbon. Here, the activated carbon may be used in powder form, granule form or as cylindrically formed particles. In this connection, the activated carbon is advantageously used in granule form (granular activated carbon) in fixed- or fluidized-bed filters. Examples of preferred carbons are the activated carbons CPG(R) LF, CAL (R) and APC(R) from Chemviron Carbon. Further details on properties and grades of the activated carbons used are given in Ullmann's Encyclopedia, Sixth Edition, 2000 Electronic Release, Chapter 5.

The amount of adsorbent used is preferably selected in the range of 0.001 to 0.2 g, preferably 0.05 to 0.1 g, based in each case on 1 g of the 2-phenyl-1,3-benzoxazole of formula (I) to be decolorized.

A particularly preferred embodiment of the decolorization using activated carbon comprises a.) dissolving the 2-phenyl-1,3-benzoxazole of formula (I) in an aliphatic hydrocarbon solvent such as in particular hexane, heptane or cyclohexane, at a temperature selected in the range of 30° C. to 120° C., preferably in the range of 60° C. to 110° C., particularly preferably in the range of 70° C. to 90° C., b.)

adding the activated carbon and c.) passing this solution over a pre-heated sand-cored funnel.

The aliphatic hydrocarbon solvent in the decolorization step is preferably selected from the group consisting of pentane, hexane, heptane or cyclohexane, more preferably from hexane or heptane. Most preferably the solvent is heptane.

The process according to the invention also comprises crystallizing the 2-phenyl-1,3-benzoxazole of formula (I) from the aliphatic hydrocarbon solution.

EXAMPLE 1

Preparation of 4-Fluoro-N-(2-hydroxyphenyl)-benzamide (IVa)

The examples below serve to illustrate the process according to the invention in more detail. 4-fluorobenzoic chloride (B) was added drop wise to a mixture of 2-aminophenol (A) in the respective solvent. The concentration of the 4-fluorobenzoic chloride (B) in the solvent [g/ml] is given in table 1. Afterwards the reaction was stirred under nitrogen. The conditions and results are listed in table 1. The amount of base is given as mol-equivalents based on the amount of 4-fluorobenzoic chloride (B). The reaction mixtures were analyzed after the indicated time by HPLC (254 nm, area %) in particular for determining the amount of 4-fluoro-Benzoic acid 2-[(4-fluorobenzoyl)amino]phenyl ester (i.e. the diacylated product, DAP). Then, 4-Fluoro-N-(2-hydroxyphenyl)-benzamide (IVa) was isolated resulting in the yields as indicated in the table 1 (purity >98% (HPLC at 254 nm)).

TABLE 1

| | Mol-eq. | | | c(B) | | | T | Time | Result |
|---|---|---|---|---|---|---|---|---|---|
| | B | A | Solvent | [g/ml] | Base | | [° C.] | [h] | [%] |
| Inv 1 | 1 | 1 | Toluene | 0.08 | NaHCO$_3$, 1.1 eq | | 10-20 | 1.5 | 94% (IVa) |
| Inv 2 | 1 | 1 | Xylene | 0.08 | NaHCO$_3$, 1.1 eq | | 10-20 | 2.5 | 98% (IVa) |
| Inv 3 | 1 | 1 | Toluene | 0.13 | NaHCO$_3$, 1.1 eq | | 10-20 | 10 | 96% (IVa) |
| Inv 4 | 1 | 1 | Toluene | 0.25 | NaHCO$_3$, 1.1 eq | | 10-20 | 14 h | 96% (IVa) |
| Inv 6 | 1 | 1 | THF | 0.32 | NaHCO$_3$, 1.1 eq | | 10-20 | 1.8 | 97% (IVa) |
| Inv 7 | 1 | 1 | THF | 0.42 | NaHCO$_3$, 1.1 eq | | 10-20 | 14 | 99% (IVa) |
| Inv 8 | 1 | 1 | 2-MTHF | 0.2 | NaHCO$_3$, 1.1 eq | | 10-20 | 2.5 | 99% (IVa) |
| Ref 1 | 1 | 1 | Toluene | 0.2 | NaHCO$_3$, 0.5 eq | | 10-20 | 2 | only DAP |
| Ref 2 | 1 | 1 | THF | 0.2 | Et$_3$N, 1.4 eq. | | 20 | 10 | only DAP |
| Ref 3 | 1.1 | 1 | THF | 0.2 | Et$_3$N, 1.2 eq. | | 0 | 4 | 50% (IVa) 50% DAP |
| Ref 4 | 1.1 | 1 | THF | 0.2 | Et$_3$N, 1.2 eq. | | −10 | 3 | 50% (IVa) 50% DAP |
| Ref 5 | 1.1 | 1 | THF | 0.2 | Et$_3$N, 1.2 eq. | | 40 | 4 | 64% (IVa) 36% DAP |
| Ref 6 | 1 | 1 | Toluene | 0.2 | Na$_2$CO$_3$, 1 eq | | 10-20 | 1 | only DAP |
| Ref 7 | 1 | 1 | Toluene | 0.08 | none | | 110 | 4 | 57% (IVa) |
| Ref 8 | 1 | 1 | Toluene | 0.25 | none | | 20 | 7 | mixture of products |

From table 1 it can be seen that the use Et$_3$N, Na$_2$CO$_3$ or the reaction without a base led to significant amounts of DAP or mixtures of products while the reaction of equal amount of 4-fluorobenzoic chloride and 2-aminophenol with >0.75 eq of NaHCO$_3$ resulted in high yields (>95%).

EXAMPLE 2

Preparation of 2(4-fluorophenyl)-1,3-benzoxazole

4-Fluoro-N-(2-hydroxyphenyl) benzamide (IVa), acid (H$_2$SO$_4$, methanesulfonic acid (MeSO$_3$H) or p-toluene sulfonic acid (p-TsOH)) and solvent were heated under the conditions outlined in table 2 with a Dean-Stark tube.

TABLE 2

| | Acid | Solvent & c (IVa) | T [° C.] | Time [h] | Yield [%] |
|---|---|---|---|---|---|
| 1 | p-TsOH, 2 eq | Xylene, 0.1 g/ml | 140 | 7 | 88 |
| 2 | H$_2$SO$_4$, 2 eq | Xylene, 0.1 g/ml | 140 | 4 | 35 |
| 3 | p-TsOH, 0.2 eq | Xylene, 0.34 g/ml | 140 | 3 | 95 |
| 4 | H$_2$SO$_4$, 0.2 eq | Toluene, 0.1 g/ml | 110 | 8 | 72 |
| 5 | p-TsOH, 1 eq | Toluene, 0.1 g/ml | 110 | 3 | 93 |
| 6 | p-TsOH, 0.2 eq | Toluene, 0.2 g/ml | 110 | 6.5 | 99 |
| 7 | p-TsOH, 0.1 eq | Toluene, 0.2 g/ml | 110 | 14 | 95 |
| 8 | p-TsOH, 0.05 eq | Toluene, 0.4 g/ml | 110 | 23 | 98 |
| 9 | p-TsOH, 0.3 eq | Toluene, 0.4 g/ml | 110 | 5 | 97 |
| 11 | MeSO$_3$H, 0.2 eq | Toluene, 0.2 g/ml | 110 | 14 | 99 |
| 10 | p-TsOH, 0.25 eq | 2-MTHF, 0.25 g/ml | 80 | 8 hrs. | 20 |

As can be retrieved from table 2, various cyclization methods can be applied to form the 2-(4-fluorophenyl)-1,3-benzoxazole. However, using no more than 0.3 mole-equivalents of p-TsOH and MeSO$_3$H as catalyst in a solvent which forms an azeotrop with water such as toluene and xylene resulted in the highest yield (>95%).

The optimized condition for cyclization is 0.2-0.4 g/ml amide in Toluene with 0.2-0.3 eq of p-TsOH, the refluxing time is 6-8 hours.

EXAMPLE 3

Two-Step Synthesis of 2-(4-fluorophenyl)-1,3-benzoxazole

Step 1: Preparation of 4-Fluoro-N-(2-hydroxyphenyl)-benzamide

To a 500 ml 4 necked round bottom flask equipped with a thermometer, a mechanic stirrer, a drop funnel, a nitrogen in-let, was added sodium bicarbonate (29.6 g, 0.354 mol, 1.1 eq), 2-aminophenol (34.88 g, 0.32 mol, 1 eq) and 2-Methyl THF (250 ml). The temperature of the mixture was controlled under 20° C. by ice-bath. Under vigorously stirring, 4-fluorobenzoyl chloride (50.72 g, 0.32 mol, 1 eq) was added drop wise within 10 min. Then the reaction was allowed to be stirred for another 1.5 hrs. When HPLC data showed that less than 0.3% of 2-aminophenol remained, 100 ml of water and 50 ml of 2-methyl tetrahydrofuran was added to quench the reaction and then the mixture was heated to 60° C. with stirring. The mixture was partitioned into two phases and the organic phase was washed with 100 ml of 1N $H_2SO_4$ and subsequently with 100 ml of water. Then the solvent was evaporated to almost dryness with stirring.

Solvent Exchange:

Toluene (250 ml) was added in the flask with stirring, which was then heated to 70° C. and the solvents were distilled off at 600 mbar, after vacuum was released, toluene (300 ml) was added and the oil bath temperature was raised to 120° C. After about 50 ml toluene distilled off, the vapor temperature increased to 110° C., which is the boiling point of toluene, indicating the completion of the solvent exchange.

Step 2: Preparation of
2-(4-fluorophenyl)-1,3-benzoxazole

After the flask containing 4-Fluoro-N-(2-hydroxyphenyl)-benzamide in 250 ml of toluene of step 1 was equipped with a Dean-Stark apparatus, p-toluenesulfonic acid (12.2 g, 64 mmol, 0.2 eq) was added. The mixture was stirred at 110° C. for 8 hours. Then heating was stopped and the solution was subsequently washed with 100 ml of water, 2*100 ml of (0.2M) NaOH solution and 100 ml of water. Toluene was removed via rotary evaporator yielding 64 g (94%) of slightly off white 2-(4-fluorophenyl)-1,3-benzoxazole.

Decolorization:

To a 1000 ml round bottom flask was added crude product (64 g) and heptane (450 ml), then the mixture was heated to 80° C. Active carbon (7 g) was then added, the mixture was stirred at this temperature for 15 minutes followed by filtration through a pre-heated 4G sand-cored funnel. The filtrate was concentrated to about 250 ml and then gradually cooled to −15° C. whereby 2-(4-fluorophenyl)-1,3-benzoxazole crystallized. The white solid was filtered and dried under vacuum yielding 56 g of white 2-(4-fluorophenyl)-1,3-benzoxazole (87% overall yield).

The invention claimed is:

1. Process for producing 2-phenyl-1,3-benzoxazoles of formula (I),

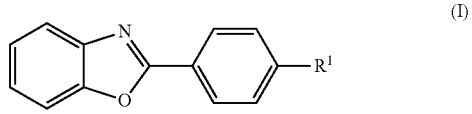

wherein
$R^1$ is hydrogen, $C_1$-$C_6$-alkyl, halogen, OH or $OR^2$; and
$R^2$ is $C_1$-$C_6$-alkyl, propargyl or allyl,
said process comprising the steps of
(i) reacting 2-aminophenol (II) with a benzoyl chloride of formula (III) to the amide of formula (IV)

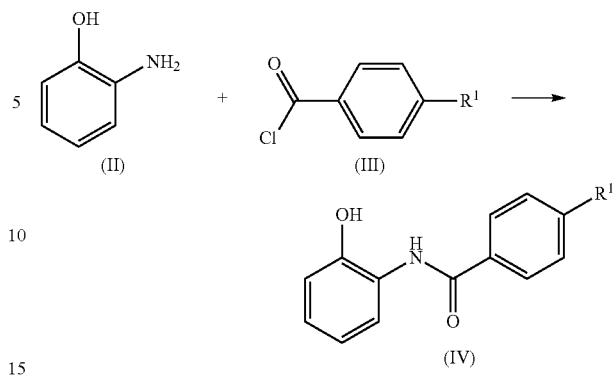

10 followed by
(ii) cyclisation of the amide (IV) to 2-phenyl-1,3-benzoxazol of formula (I),
wherein step (i) is carried out in an inert organic solvent in the presence of at least 0.75 mole-equivalent of sodium hydrogen carbonate or potassium hydrogen carbonate based on the benzoyl chloride of formula (III).

2. A process according to claim 1, wherein $R^1$ denotes to a linear $C_1$-$C_4$-alkyl radical, to $OR^2$ wherein $R^2$ is a propargyl or an allyl radical, or to a fluor radical.

3. A process according to claim 2, wherein $R^1$ is a fluor radical.

4. A process according to claim 1, wherein the inert solvent is selected from the group consisting of toluene, xylene, dioxane, tetrahydrofuran or 2-methyl-tetrahydrofurane.

5. A process according to claim 1, wherein the inert solvent is 2-methyltetrahydrofuran.

6. A process according to claim 1, wherein the amount of the inert solvent is selected such that the amount of the benzoyl chloride of formula (III) is in the range of 0.001-2 g/ml solvent, preferably in the range of 0.01-1 g/ml solvent, most preferably in the range of 0.1-0.5 g/ml.

7. A process according to claim 1, wherein the amount of sodium or potassium hydrogen carbonate is selected in the range of 0.75-1.5 mole-equivalents based on the amount of the benzoyl chloride of formula (III).

8. A process according to claim 1, wherein sodium hydrogen carbonate is used.

9. A process according to claim 1, wherein the molar ratio of aminophenol (II) to benzoylchloride (III) is selected in the range of 0.75-1.25, such as more preferably in the range of 0.9-1.1.

10. A process according to claim 1, wherein the amide (IV) is isolated before the cyclisation step.

11. A process according to claim 1, wherein the cyclization is carried out in toluene or xylene in the presence of an acidic catalyst selected from the group consisting of methanesulfonic acid and/or p-toluenesulfonic acid.

12. A process according to claim 11, wherein the reaction water formed during the cyclization is removed by azeotrop distillation.

13. A process according to claim 1, wherein the process comprises after the cyclization step (ii) an additional decolorization step.

14. A process according to claim 13, wherein the decolorization is done by treatment with activated charcoal.

* * * * *